US009655529B2

(12) United States Patent
Aoki et al.

(10) Patent No.: US 9,655,529 B2
(45) Date of Patent: May 23, 2017

(54) LEFT ATRIAL PRESSURE MEASUREMENT METHOD AND LEFT ATRIAL PRESSURE MEASUREMENT DEVICE

(71) Applicants: SEIKO EPSON CORPORATION, Tokyo (JP); NATIONAL CEREBRAL AND CARDIOVASCULAR CENTER, Suita-shi, Osaka (JP)

(72) Inventors: Mikio Aoki, Suwa (JP); Kazunori Uemura, Ibaraki (JP); Masaru Sugimachi, Toyonaka (JP)

(73) Assignees: SEIKO EPSON CORPORATION, Tokyo (JP); NATIONAL CEREBRAL AND CARDIOVASCULAR CENTER, Suita (JP)

( * ) Notice: Subject to any disclaimer, the term of this patent is extended or adjusted under 35 U.S.C. 154(b) by 627 days.

(21) Appl. No.: 14/174,329

(22) Filed: Feb. 6, 2014

(65) Prior Publication Data
US 2014/0228683 A1     Aug. 14, 2014

(30) Foreign Application Priority Data

Feb. 12, 2013 (JP) ................................. 2013-024296

(51) Int. Cl.
| A61B 8/00 | (2006.01) |
| A61B 5/021 | (2006.01) |
| A61B 8/04 | (2006.01) |
| A61B 8/08 | (2006.01) |

(52) U.S. Cl.
CPC .............. *A61B 5/021* (2013.01); *A61B 8/48* (2013.01); *A61B 8/488* (2013.01); *A61B 8/5223* (2013.01); *A61B 8/04* (2013.01); *A61B 8/0883* (2013.01)

(58) Field of Classification Search
None
See application file for complete search history.

(56) References Cited

U.S. PATENT DOCUMENTS

2008/0139958 A1     6/2008   Uemura et al.

FOREIGN PATENT DOCUMENTS

| JP | A-2006-142038 | 6/2006 |
| JP | A-2008-168120 | 7/2008 |
| WO | WO 98/19593 A1 | 5/1998 |
| WO | WO 2006/022873 A2 | 3/2006 |
| WO | WO 2009/111789 A2 | 9/2009 |

OTHER PUBLICATIONS

Drazner et al. "Value of Clinician Assessment of Hemodynamics in Advanced Heart Failure", *Circulation Heart Failure*, 2008, pp. 170-177, vol. 1.

(Continued)

*Primary Examiner* — Amanda Lauritzen Moher
*Assistant Examiner* — Shahdeep Mohammed
(74) *Attorney, Agent, or Firm* — Oliff PLC

(57) ABSTRACT

A left atrial pressure measurement device includes: a measurement section that measures a first index value that indicates performance of a right ventricle, and a second index value that indicates performance of a left ventricle; and a calculation section that calculates a left atrial pressure using the first index value, the second index value, and a measured right atrial pressure.

9 Claims, 9 Drawing Sheets

(56) References Cited

OTHER PUBLICATIONS

Wahl et al. "Assessment of Right Ventricular Systolic Function: Comparison Between Cardiac Magnetic Resonance Derived Ejection Fraction and Pulsed-Wave Tissue Doppler Imaging of the Tricuspid Annulus", *International Journal of Cardiology*, 2011, pp. 58-62, vol. 151.

Gulati et al. "Mitral Annular Descent Velocity by Tissue Doppler Echocardiography as an Index of Global Left Ventricular Function", *American Journal of Cardiology*, 1996, pp. 979-984, vol. 77.

Klotz et al. "Single-Beat Estimation of End-Diastolic Pressure-Volume Relationship: A Novel Method with Potential for Noninvasive Application", *American Journal of Physiology Heart Circ Physiology*, 2006, pp. H403-H412, vol. 291.

Desjardins et al. "Can Peripheral Venous Pressure be Interchangeable with Central Venous Pressure in Patients Undergoing Cardiac Surgery?", *Intensive Care Med.*, 2004, pp. 627-632, vol. 30.

Bruhl et al. "A Novel Approach to Standard Techniques in the Assessment and Quantification of the Interventricular Systolic Relationship", *Cardiovascular Ultrasound*, 2011, pp. 1-5, vol. 9:42.

Nishimura, R.A. et al., "Quantitative Hemodynamics by Doppler Echocardiography: A Noninvasive Alternative to Cardiac Catheterization," *Progress in Cardiovascular Diseases*, Jan./Feb. 1994, pp. 309-342, vol. 36, No. 4.

Gorcsan, J. et al., "Noninvasive estimation of left atrial pressure in patients with congestive heart failure and mitral regurgitation by Doppler echocardiography," *American Heart Journal*, Mar. 1991, pp. 858-863, vol. 121, No. 3, Part 1.

Desjardins, R. et al., "Can peripheral venous pressure be interchangeable with central venous pressure in patients undergoing cardiac surgery?," *Intensive Care Medicine*, Apr. 1, 2004, pp. 627-632, vol. 30, No. 4.

Anavekar, N.S., et al., "Doppler echocardiography: A contemporary review," *Journal of Cardiology*, Dec. 1, 2009, pp. 347-358, vol. 54, No. 3.

Huez, S. et al., "Echocardiographic and Tissue Doppler Imaging of Cardiac Adaptation to High Altitude in Native Highlanders Versus Acclimatized Lowlanders," *The American Journal of Cardiology*, Jun. 1, 2009, pp. 1605-1609, vol. 103, No. 11.

LEFT ATRIAL PRESSURE MEASUREMENT METHOD AND LEFT ATRIAL PRESSURE MEASUREMENT DEVICE

Japanese Patent Application No. 2013-024296 filed on Feb. 12, 2013, is hereby incorporated by reference in its entirety.

BACKGROUND

It has been considered that the measurement of the left atrial pressure (LAP) is important for the evaluation of the cardiac performance in addition to the measurement of the blood pressure and the cardiac output. Therefore, various techniques for measuring the left atrial pressure have been developed. For example, a technique has been known that inserts a catheter provided with a balloon at the tip into the esophagus, inflates the balloon at a position adjacent to the left atrium, and measures the internal pressure of the balloon to measure the left atrial pressure, taking account of the fact that the esophagus is situated on the back side of the left atrium (see JP-A-2006-142038, for example).

According to the above technique, however, since it is necessary to indwell the balloon in the esophagus, the burden imposed on the subject increases.

Pulmonary artery catheterization, ultrasound Doppler echocardiography, and the like have also been known as a technique for measuring or estimating the left atrial pressure. However, these techniques also have a problem.

For example, when implementing pulmonary artery catheterization, a catheter is inserted into the pulmonary artery through the jugular vein and the right atrium. The blood flow is temporarily blocked by wedging a balloon provided just proximal to the tip of the catheter into the pulmonary artery, and the static pressure applied to the end of the catheter is measured. The static pressure (i.e., pulmonary capillary wedge pressure (PCWP)) thus measured is used as a substitute for the left atrial pressure (LAP). This technique achieves high measurement accuracy, but is very invasive. Moreover, skill is required for the operator to insert the catheter into an appropriate position.

Ultrasound Doppler echocardiography (transthoracic ultrasound Doppler echocardiography) is a technique that estimates the left atrial pressure (LAP) using the ratio (E/e') of the early diastolic peak (E) of the mitral valve orifice blood flow waveform to the early diastolic peak (e') of the mitral annulus motion velocity waveform. However, recent studies have revealed that the ratio (E/e') does not necessarily have a correlation with the pulmonary capillary wedge pressure (PCWP) in various cardiac diseases.

SUMMARY

According to one aspect of the invention, there is provided a left atrial pressure measurement method comprising:
measuring a first index value that indicates performance of a right ventricle;
measuring a second index value that indicates performance of a left ventricle; and
calculating a left atrial pressure using the first index value, the second index value, and a measured right atrial pressure.

According to another aspect of the invention, there is provided a left atrial pressure measurement device comprising:
a measurement section that measures a first index value that indicates performance of a right ventricle, and a second index value that indicates performance of a left ventricle; and
a calculation section that calculates a left atrial pressure using the first index value, the second index value, and a measured right atrial pressure.

DESCRIPTION OF EXEMPLARY EMBODIMENTS

Figure 1:
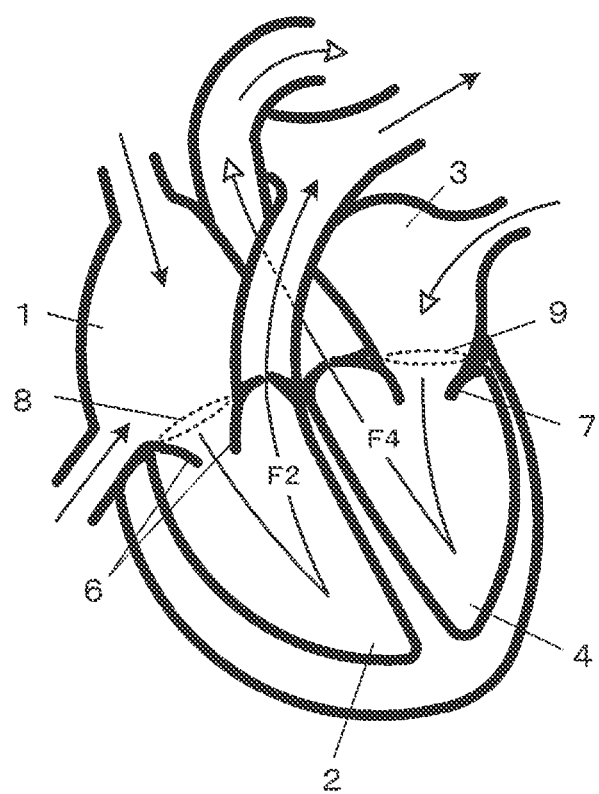
FIG. 1 is a schematic cross-sectional view illustrating a heart.

Several embodiments of the invention may implement novel left atrial pressure (LAP) measurement technology.

According to one embodiment of the invention, there is provided a left atrial pressure measurement method comprising:
measuring a first index value that indicates performance of a right ventricle;
measuring a second index value that indicates performance of a left ventricle; and
calculating a left atrial pressure using the first index value, the second index value, and a measured right atrial pressure.

According to another embodiment of the invention, there is provided a left atrial pressure measurement device comprising:
a measurement section that measures a first index value that indicates performance of a right ventricle, and a second index value that indicates performance of a left ventricle; and
a calculation section that calculates a left atrial pressure using the first index value, the second index value, and a measured right atrial pressure.

In the left atrial pressure measurement method,
the calculating of the left atrial pressure may include:
calculating a relative ratio of the first index value to the second index value; and
calculating the left atrial pressure using the relative ratio and the right atrial pressure.

According to the above configuration, the left atrial pressure can be estimated from the first index value that indicates the performance of the right ventricle, and the second index value that indicates the performance of the left ventricle.

In the left atrial pressure measurement method,
the measuring of the first index value may include measuring a velocity of a tricuspid annulus to determine the first index value, and
the measuring of the second index value may include measuring a velocity of a mitral annulus to determine the second index value.

In the left atrial pressure measurement method,
the measuring of the first index value may include measuring the velocity of the tricuspid annulus due to pulsation using ultrasonic waves to determine a maximum value or an average value measured during systole to be the first index value, and
the measuring of the second index value may include measuring the velocity of the mitral annulus due to pulsation using ultrasonic waves to determine a maximum value or an average value measured during systole to be the second index value.

In the left atrial pressure measurement method,
the measuring of the first index value may include measuring an acceleration of a tricuspid annulus to determine the first index value, and
the measuring of the second index value may include measuring an acceleration of a mitral annulus to determine the second index value.

In the left atrial pressure measurement method,
the measuring of the first index value may include measuring the acceleration of the tricuspid annulus due to pulsation using ultrasonic waves to determine a maximum value or an average value measured during systole to be the first index value, and
the measuring of the second index value may include measuring the acceleration of the mitral annulus due to pulsation using ultrasonic waves to determine a maximum value or an average value measured during systole to be the second index value.

The velocity and the acceleration of the tricuspid annulus and the mitral annulus can be measured using ultrasound Doppler echocardiography. Therefore, the left atrial pressure can be measured less-invasively.

In the left atrial pressure measurement method,
the measuring of the first index value may include continuously measuring displacement of the tricuspid annulus due to pulsation using ultrasonic waves to continuously measure the first index value,
the measuring of the second index value may include continuously measuring displacement of the mitral annulus due to pulsation using ultrasonic waves to continuously measure the second index value, and
the calculating of the left atrial pressure may include continuously calculating the left atrial pressure using the first index value and the second index value.

The left atrial pressure measurement method may further comprise:
measuring the displacement of the tricuspid annulus and the displacement of the mitral annulus using an ultrasonic sensor section attached to a skin surface.

The displacement of the tricuspid annulus and the mitral annulus can be measured using ultrasound Doppler echocardiography. Therefore, the left atrial pressure can be measured less-invasively.

The left atrial pressure measurement method may further comprise:
measuring a jugular venous pressure or a peripheral venous pressure; and
determining the right atrial pressure from the measured jugular venous pressure or peripheral venous pressure.

The jugular venous pressure or the peripheral venous pressure can be measured non-invasively.

Therefore, the right atrial pressure can be measured non-invasively.

Exemplary embodiments to which the invention is applied are described below with reference to the drawings. Note that the embodiments to which the invention may be applied are not limited to the following exemplary embodiments.

The left atrial pressure estimation principle according to the embodiments of the invention is described below.

FIG. 1 is a schematic view illustrating the structure of a heart. Blood is pumped out from the heart, flows through the whole body or the lungs, and returns to the heart (circulation cycle). Therefore, the blood flow F2 that flows out from the right ventricle 2 and the blood flow F4 that flows out from the left ventricle 4 are considered to be equal. The left atrial pressure (LAP) is a filling pressure applied to the left ventricle 4, and the right atrial pressure (RAP) is a filling pressure applied to the right ventricle 2. The blood flow from the ventricle increases when the atrial pressure increases.

The relationship between the ventricular performance and the atrial pressure is described below. A ventricle having excellent performance can pump out a given amount of blood at a low atrial pressure, while a ventricle having decreased performance requires a high atrial pressure in order to pump out a given amount of blood. Therefore, when the right cardiac output and the left cardiac output are identical, the right atrial pressure should be lower than the left atrial pressure (i.e., the left atrial pressure should be higher than the right atrial pressure) when the performance of the right ventricle is relatively higher (better) than the performance of the left ventricle. The right atrial pressure should be higher than the left atrial pressure (i.e., the left atrial pressure should be lower than the right atrial pressure) when the performance of the right ventricle is relatively lower than the performance of the left ventricle.

It has been known that the peak systolic tricuspid annular velocity ($S_T$) (i.e., the peak systolic velocity (i.e., the velocity along the direction in which the tricuspid annulus 8 approaches and moves away from the ventricular apex) of the tricuspid annulus 8 that is situated at the base of the tricuspid valve 6) is highly correlated with the performance of the right ventricle (see International Journal of Cardiology 2011; 151: 58-62). Therefore, the peak systolic tricuspid annular velocity ($S_T$) can be used as an index value (first index value) that indicates the performance of the right ventricle.

It has been known that the peak systolic mitral annular velocity ($S_M$) (i.e., the peak systolic velocity (i.e., the velocity along the direction in which the mitral annulus 9 approaches and moves away from the ventricular apex) of the mitral annulus 9 that is situated at the base of the mitral valve 7) is highly correlated with the performance of the left ventricle (see American Journal of Cardiology 1996; 77: 979-984). Therefore, the peak systolic mitral annular velocity ($S_M$) can be used as an index value (second index value) that indicates the performance of the left ventricle.

Accordingly, the relationship between the performance of the right ventricle and the performance of the left ventricle can be expressed by the ratio "first index value/second index value" (i.e., "$S_T/S_M$"), and the left atrial pressure can be accurately estimated when the right atrial pressure and the ratio "$S_T/S_M$" are known.

The above principle can be explained as below based on the physiological relationship between the left atrial pressure, the right atrial pressure, and the ratio "$S_T/S_M$".

Specifically, the peak systolic tricuspid annular velocity ($S_T$) has a linear correlation with the performance of the right ventricle, e.g., the ejection fraction (EF) (=stroke volume/ventricular end-diastolic volume) of the right ventricle. The peak systolic mitral annular velocity ($S_M$) has a linear correlation with the performance of the left ventricle, e.g., the ejection fraction (EF) of the left ventricle. Therefore, the peak systolic tricuspid annular velocity ($S_T$) and the peak systolic mitral annular velocity ($S_M$) can be given by the following expressions (A) and (B), respectively.

$$S_T = \alpha_R \cdot \text{right ventricular stroke volume/right ventricular end-diastolic volume} \quad (A)$$

$$S_M = \alpha_L \cdot \text{left ventricular stroke volume/left ventricular end-diastolic volume} \quad (B)$$

where, $\alpha_R$ and $\alpha_L$ are proportional constants.

Since the left ventricular stroke volume and the right ventricular stroke volume are identical in an equilibrium state, the following expression (C) can be obtained from the expressions (A) and (B).

$$\text{Left ventricular end-diastolic volume} = \alpha_{L/R} \cdot (S_T/S_M) \cdot \text{right ventricular end-diastolic volume} \quad (C)$$

where, $\alpha_{L/R}$ is a proportional constant ($\alpha_L/\alpha_R$).

It has been known that the relationship between the diastolic volume and the diastolic pressure of the right ventricle and the left ventricle can be approximated by the following expressions (D) and (E), respectively (see American Journal of Physiology 2006; 291: H403-412).

$$\text{Right ventricular end-diastolic pressure} = A_R \cdot \text{right ventricular end-diastolic volume}^{BR} \quad (D)$$

$$\text{Left ventricular end-diastolic pressure} = A_L \cdot \text{left ventricular end-diastolic volume}^{BL} \quad (E)$$

where, $A_R$, $A_L$, BR, and BL are constants, and BR and BL are exponents.

The right ventricular end-diastolic pressure and the left ventricular end-diastolic pressure can be given by the following expressions (F) and (G), respectively.

$$\text{Right ventricular end-diastolic pressure} \approx \text{right atrial pressure} \quad (F)$$

$$\text{Left ventricular end-diastolic pressure} \approx \text{left atrial pressure} \quad (G)$$

The left atrial pressure can be given by the following expression (H) relative to the right atrial pressure and the ratio "$S_T/S_M$" by integrating the expressions (C) to (G).

$$\ln(\text{left atrial pressure}) = C1 \cdot \ln(\text{right atrial pressure}) + C2 \cdot \ln(S_T/S_M) + C3 \quad (H)$$

C1, C2, and C3 in the expression (H) are constants calculated from $\alpha_{L/R}$, $A_R$, $A_L$, BR, and BL. In the embodiments of the invention, values regressively determined from the results of preliminary experiments described later are used as C1, C2, and C3.

Solving the expression (H) yields the following expression (J).

$$\text{Left atrial pressure} = \text{EXP}[C1 \cdot \ln(\text{right atrial pressure}) + C2 \cdot \ln(S_T/S_M) + C3] \quad (J)$$

Accordingly, the left atrial pressure can be accurately estimated using the expression (J) by measuring the right atrial pressure, the peak systolic tricuspid annular velocity ($S_T$), and the peak systolic mitral annular velocity ($S_M$).

First Embodiment

A first embodiment to which the invention is applied is described below.

Figure 2:
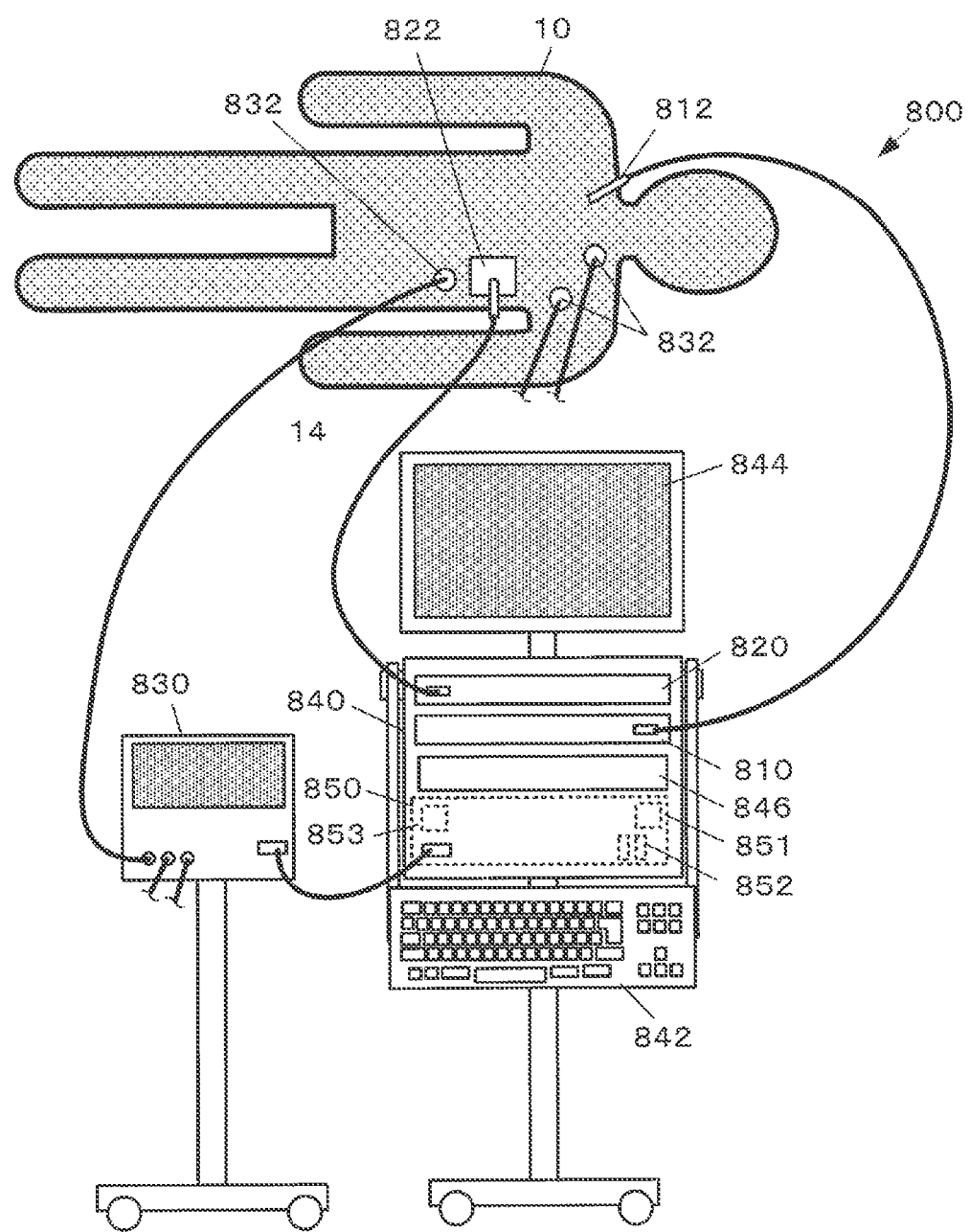
FIG. 2 is a view illustrating a system configuration example of a left atrial pressure measurement device according to a first embodiment.

FIG. 2 is a view illustrating a system configuration example of a left atrial pressure measurement device 800 according to the first embodiment. The left atrial pressure measurement device 800 according to the first embodiment is a computer system that includes (1) a jugular venous pressure measurement device 810, (2) a transthoracic echocardiographic device 820, (3) an electrocardiographic device 830, and (4) a processing device 840 that calculates (estimates) the left atrial pressure, and stores the calculated (estimated) left atrial pressure in time series.

The jugular venous pressure measurement device 810 according to the first embodiment is a known device that measures the jugular venous pressure (JVP) using a jugular venous pressure measurement catheter 812, and successively transmits the data of the jugular venous pressure to the processing device 840.

The transthoracic echocardiographic device 820 is an echocardiographic device. The transthoracic echocardiographic device 820 applies measurement ultrasonic waves from a transthoracic ultrasonic probe 822, and converts reflected waves (ultrasonic echo) from a subject 10 into electrical signals. The attachment position of the transthoracic ultrasonic probe 822 is adjusted so that the tricuspid annulus 8 and the mitral annulus 9 are insonated.

The transthoracic echocardiographic device 820 according to the first embodiment is configured so that the operator can designate a position within an echo screen displayed on a touch panel 844 using a cursor. The transthoracic echocardiographic device 820 can continuously calculate the displacement amount, the displacement velocity, and the acceleration at the position designated using the cursor. Specifically, the operator designates the position of the tricuspid annulus 8 and the mitral annulus 9 using the cursor. The transthoracic echocardiographic device 820 cyclically extracts the peak value in the pulsation cycle from the velocity at each position designated using the cursor by utilizing a tissue Doppler technique to calculate the peak systolic tricuspid annular velocity ($S_T$) and the peak systolic mitral annular velocity ($S_M$), and successively transmits the data of the peak systolic tricuspid annular velocity ($S_T$) and the peak systolic mitral annular velocity ($S_M$) to the processing device 840. The transthoracic echocardiographic device 820 also transmits the heart rate and the data of the velocity waveforms of the tricuspid annulus 8 and the mitral annulus 9.

The transthoracic ultrasonic probe 822 according to the first embodiment is a thin and flat pad-type ultrasonic probe that can be attached to the chest of the subject 10. In the example illustrated in FIG. 2, one transthoracic echocardiographic device 820 is provided. Note that a plurality of transthoracic echocardiographic devices 820 (e.g., a transthoracic echocardiographic device 820 that calculates the peak systolic tricuspid annular velocity ($S_T$), and a transthoracic echocardiographic device 820 that calculates the peak systolic mitral annular velocity ($S_M$)) may be used.

The electrocardiographic device 830 measures an electrocardiogram using an electrode 832 attached to the chest of the subject 10, and outputs the heart rate to the processing device 840. Note that the electrocardiographic device 830 may be implemented by the jugular venous pressure measurement device 810 or the transthoracic echocardiographic device 820. When the electrocardiographic device 830 is implemented by the transthoracic echocardiographic device 820, the electrocardiographic device 830 may detect the pulsation cycle from the time-series waveforms of the velocity of the tricuspid annulus 8 and the velocity of the mitral annulus 9 to measure the heart rate, for example.

The processing device 840 includes a keyboard 842 (swing-up-type keyboard in the example illustrated in FIG. 2), the touch panel 844, a data logger 846, and a control board 850.

The control board 850 is implemented by a microprocessor (e.g., central processing unit (CPU) 851, graphics processing unit (GPU), or digital signal processor (DSP)), an application-specific integrated circuit (ASIC), an electronic circuit, a storage medium such as an IC memory 852 (e.g., VRAM, RAM, or ROM) or a hard disk, an interface IC that implements data transfer with the outside, a connection terminal, a power supply circuit, a communication device 853, and the like. The communication device 853 performs data communication with the transthoracic echocardiographic device 820, the electrocardiographic device 830, and the like, and receives the data pertaining to the jugular venous pressure, the peak systolic tricuspid annular velocity ($S_T$), the peak systolic mitral annular velocity ($S_M$), and the like.

The control board 850 executes a program stored in the storage medium (e.g., IC memory 852 or hard disk), successively calculates the left atrial pressure from the value measured by the jugular venous pressure measurement device 810 and input from the keyboard 842 or the touch panel 844, and the peak systolic tricuspid annular velocity ($S_T$) and the peak systolic mitral annular velocity ($S_M$) acquired from the transthoracic echocardiographic device 820, and stores the calculated left atrial pressure in the data logger 846 in time series.

Functional Block Diagram

Figure 3:
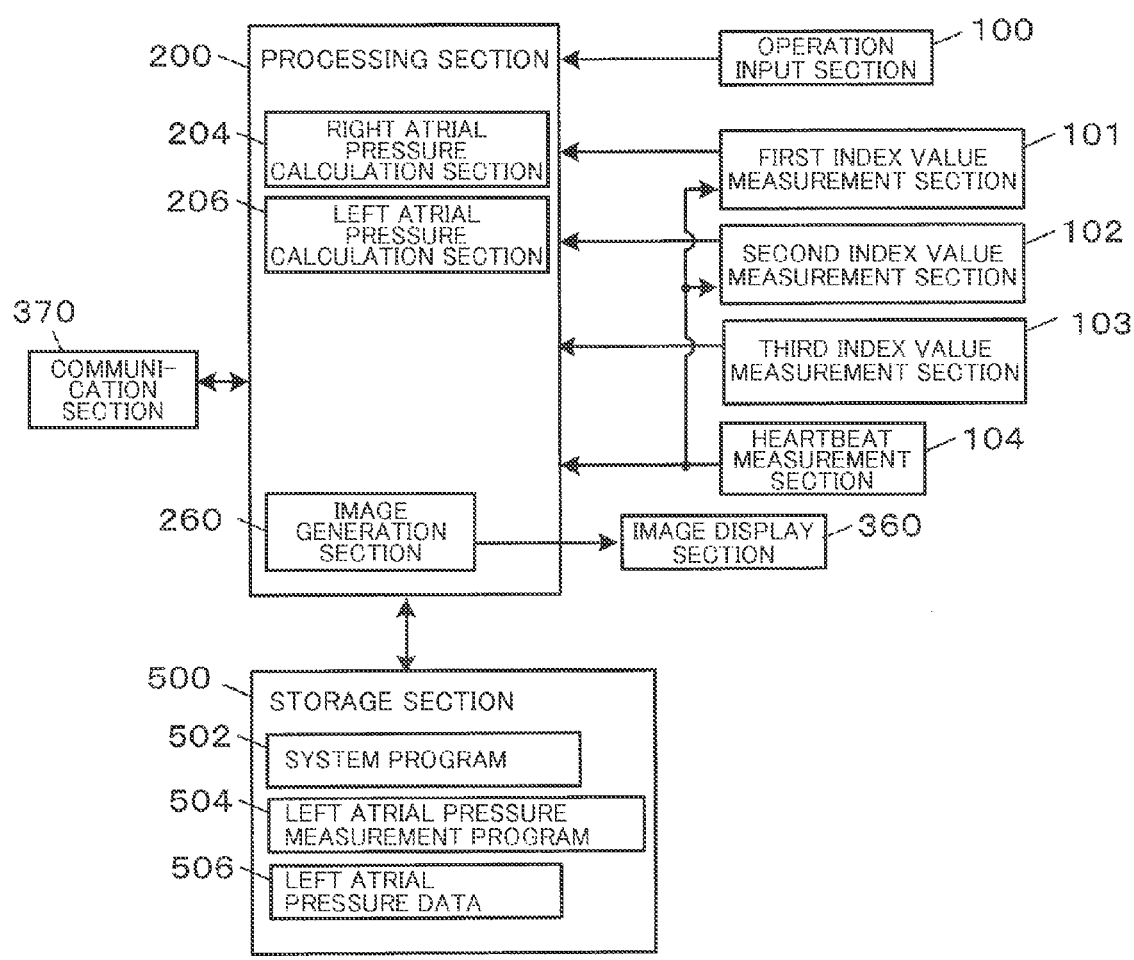
FIG. 3 is a functional block diagram illustrating a functional configuration example of the left atrial pressure measurement device according to the first embodiment.

FIG. 3 is a functional block diagram illustrating a functional configuration example of the left atrial pressure measurement device 800 according to the first embodiment. The left atrial pressure measurement device 800 includes an operation input section 100, a first index value measurement section 101, a second index value measurement section 102, a third index value measurement section 103, a processing section 200, a communication section 370, and a storage section 500.

The operation input section 100 allows the operator to perform an operation input and a value input on the left atrial pressure measurement device 800, and outputs the input signals to the processing section 200. The operation input section 100 is implemented by an input device (e.g., keyboard (hardware keyboard or software keyboard), switch, lever, or CCD module). In the first embodiment, the keyboard 842 and the touch panel 844 illustrated in FIG. 2 correspond to the operation input section 100.

The first index value measurement section 101 cyclically calculates a first index value that indicates the right ventricular function while performing a measurement control process, and outputs the first index value to the processing section 200. In the first embodiment, the transthoracic echocardiographic device 820 illustrated in FIG. 2 corresponds to the first index value measurement section 101. The first index value measurement section 101 measures the velocity of the tricuspid annulus 8, calculates the peak systolic tricuspid annular velocity ($S_T$) as the first index value, and outputs the first index value to the processing section 200.

The second index value measurement section 102 cyclically calculates a second index value that indicates the left ventricular function while performing a measurement control process, and outputs the second index value to the processing section 200. In the first embodiment, the transthoracic echocardiographic device 820 illustrated in FIG. 2 corresponds to the second index value measurement section 102. The second index value measurement section 102 measures the velocity of the mitral annulus 9, calculates the peak systolic mitral annular velocity ($S_M$) as the second index value, and outputs the second index value to the processing section 200.

The third index value measurement section 103 cyclically calculates a third index value that is highly correlated with the right atrial pressure while performing a measurement control process, and outputs the third index value to the processing section 200. In the first embodiment, the jugular venous pressure measurement device 810 illustrated in FIG. 2 corresponds to the third index value measurement section 103. The third index value measurement section 103 measures the jugular venous pressure, and outputs the jugular venous pressure to the processing section 200 as the third index value.

A heartbeat measurement section 104 continuously measures the heartbeat, and outputs the measured heartbeat to the processing section 200. In the first embodiment, the electrocardiographic device 830 illustrated in FIG. 2 corresponds to the heartbeat measurement section 104.

The processing section 200 performs various calculation processes by executing a given program, and controls the operation of the left atrial pressure measurement device 800. In the first embodiment, the processing section 200 includes a right atrial pressure calculation section 204, a left atrial pressure calculation section 206, and an image generation section 260. The control board 850 illustrated in FIG. 2 corresponds to the processing section 200.

The right atrial pressure calculation section 204 calculates (estimates) the right atrial pressure from the third index value that is highly correlated with the right atrial pressure. In the first embodiment, the right atrial pressure calculation section 204 calculates the right atrial pressure from the jugular venous pressure (JVP). The right atrial pressure may be calculated appropriately referring to Drazner et al. "Value of clinician assessment of hemodynamics in advanced heart failure", Circ Heart Fail, 2008; 1: 170-177.

The left atrial pressure calculation section 206 successively calculates the left atrial pressure based on the expression (J) from the right atrial pressure calculated by the right atrial pressure calculation section 204, the peak systolic tricuspid annular velocity ($S_T$) acquired by the first index value measurement section 101, and the peak systolic mitral annular velocity ($S_M$) acquired by the second index value measurement section 102, and stores the calculated left atrial pressure in the storage section 500 in time series as left atrial pressure data 506.

The image generation section 260 generates an image that indicates the left atrial pressure measurement results in time series, and outputs the display signals of the image to the image display section 360.

The image display section 360 is implemented by an image display device such as a flat panel display, and displays the information that is being monitored as an image. The touch panel 844 illustrated in FIG. 2 corresponds to the image display section 360.

The storage section 500 is implemented by a storage medium (e.g., IC memory or hard disk). The data logger 846 and the IC memory 852 illustrated in FIG. 2 correspond to the storage section 500.

The storage section 500 according to the first embodiment stores a system program 502, a left atrial pressure measurement program 504, and the left atrial pressure data 506. The storage section 500 also serves as a data storage area shared by each functional section.

The system program 502 is a basic program that causes the processing section 200 to function as a computer. Each functional section included in the processing section 200 can be implemented by causing the processing section 200 to execute the left atrial pressure measurement program 504 in a state in which the system program 502 is executed.

Flow of Process

Figure 4:
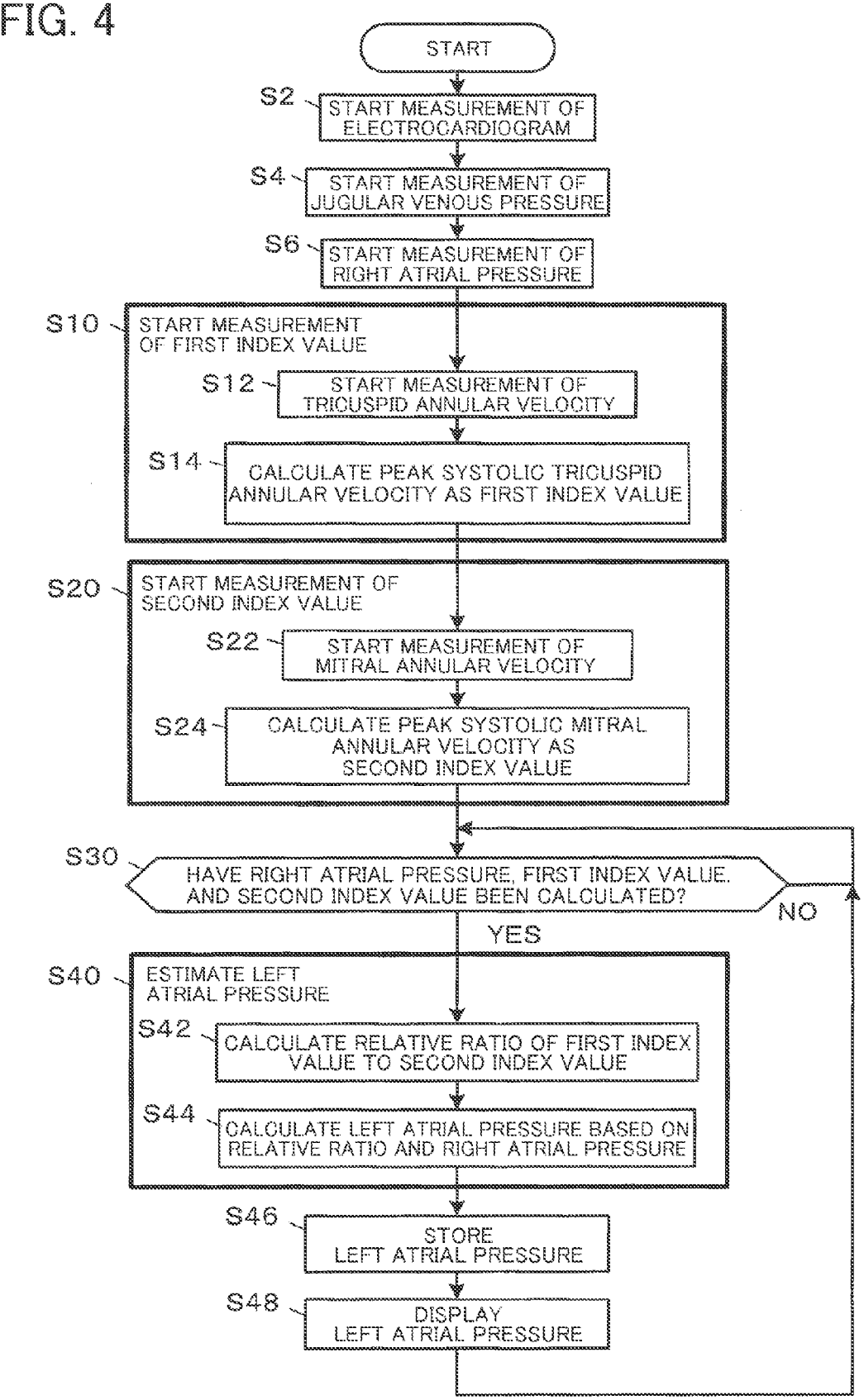
FIG. 4 is a flowchart illustrating the flow of a process performed by the left atrial pressure measurement device according to the first embodiment.

FIG. 4 is a flowchart illustrating the flow of a left atrial pressure measurement process performed by the left atrial pressure measurement device 800 according to the first embodiment. The left atrial pressure measurement process is implemented by causing the processing section 200 to execute the left atrial pressure measurement program 504.

In a step S2, the left atrial pressure measurement device 800 starts measurement of the electrocardiogram using the electrocardiographic device 830, and outputs a heartbeat timing signal and heart rate data to the transthoracic echocardiographic device 820 and the processing device 840. When the electrocardiographic device 830 is provided independently, the left atrial pressure measurement device 800 causes the electrocardiographic device 830 to start measurement of the electrocardiogram, and output the heartbeat timing signal and the heart rate data to the transthoracic echocardiographic device 820 and the processing device 840 that are connected through a communication cable.

In a step S4, the left atrial pressure measurement device 800 starts measurement of the jugular venous pressure using the jugular venous pressure measurement device 810, and outputs the measured data. In a step S6, the left atrial pressure measurement device 800 starts calculation of the right atrial pressure using the processing device 840.

In a step S10, the left atrial pressure measurement device 800 starts measurement of the first index value using the transthoracic echocardiographic device 820, and outputs the measured data. Specifically, the left atrial pressure measurement device 800 starts measurement of the tricuspid annular velocity (step S12), detects the peak systolic tricuspid annular velocity ($S_T$) of the measured tricuspid annular velocity, and outputs the peak systolic tricuspid annular velocity ($S_T$) to the processing device 840 (step S14).

In a step S20, the left atrial pressure measurement device 800 starts measurement of the second index value using the transthoracic echocardiographic device 820, and outputs the measured data. Specifically, the left atrial pressure measurement device 800 starts measurement of the mitral annular velocity (step S22), detects the peak systolic mitral annular velocity ($S_M$) of the measured mitral annular velocity, and outputs the peak systolic mitral annular velocity ($S_M$) to the processing device 840 (step S24).

Note that the step S2 (measurement of electrocardiogram), the step S4 (measurement of jugular venous pressure), the step S6 (calculation of right atrial pressure), the step S10 (measurement of first index value and output of measured data), and the step S20 (measurement of second index value and output of measured data) may be started in an arbitrary order. The subsequent process (steps S30 to S48) is performed in a state in which the steps S2 to S20 are performed in parallel.

When the right atrial pressure, the peak systolic tricuspid annular velocity ($S_T$), and the peak systolic mitral annular velocity ($S_M$) have been calculated (YES in step S30), the left atrial pressure measurement device 800 calculates (estimates) the relative ratio "$S_T/S_M$" of the first index value to the second index value, and calculates the left atrial pressure based on the relative ratio "$S_T/S_M$" and the right atrial pressure using the expression (J) (step S40).

The left atrial pressure measurement device 800 stores the calculated left atrial pressure as the left atrial pressure data 506 (step S46), generates a time-series display image of the left atrial pressure, and displays the generated display image on the touch panel 844 (step S48). The steps S30 to S48 are then repeated.

Demonstration Experiments

The following demonstration experiments were performed. In preliminary experiments, the constants C1, C2, and C3 in the expression (J) were calculated as described below. Specifically, after subjecting ten adult dogs to measurement in a normal state, some of the dogs were subjected to measurement in a state in which the left coronary artery was occluded ("left ventricular failure state"), and the remaining dogs were subjected to measurement in a state in which the pulmonary artery was occluded ("right ventricular failure state").

Each dog was simultaneously subjected to (1) measurement of the jugular venous pressure (JVP) using the jugular venous pressure measurement device 810, (2) measurement of the peak systolic tricuspid annular velocity ($S_T$) and the peak systolic mitral annular velocity ($S_M$) using the transthoracic echocardiographic device 820, and (3) measurement of the pulmonary capillary wedge pressure (PCWP) (i.e., an approximate value of the left atrial pressure) using pulmonary artery catheterization. The measured data was linked to obtain a dataset. The pulmonary capillary wedge pressure (PCWP), the jugular venous pressure (JVP), the peak systolic tricuspid annular velocity ($S_T$), and the peak systolic mitral annular velocity ($S_M$) were changed to a large extent through infusion/hemorrhage to acquire 102 datasets in total having a variation width sufficient to cover possible clinical cases.

Figure 5:
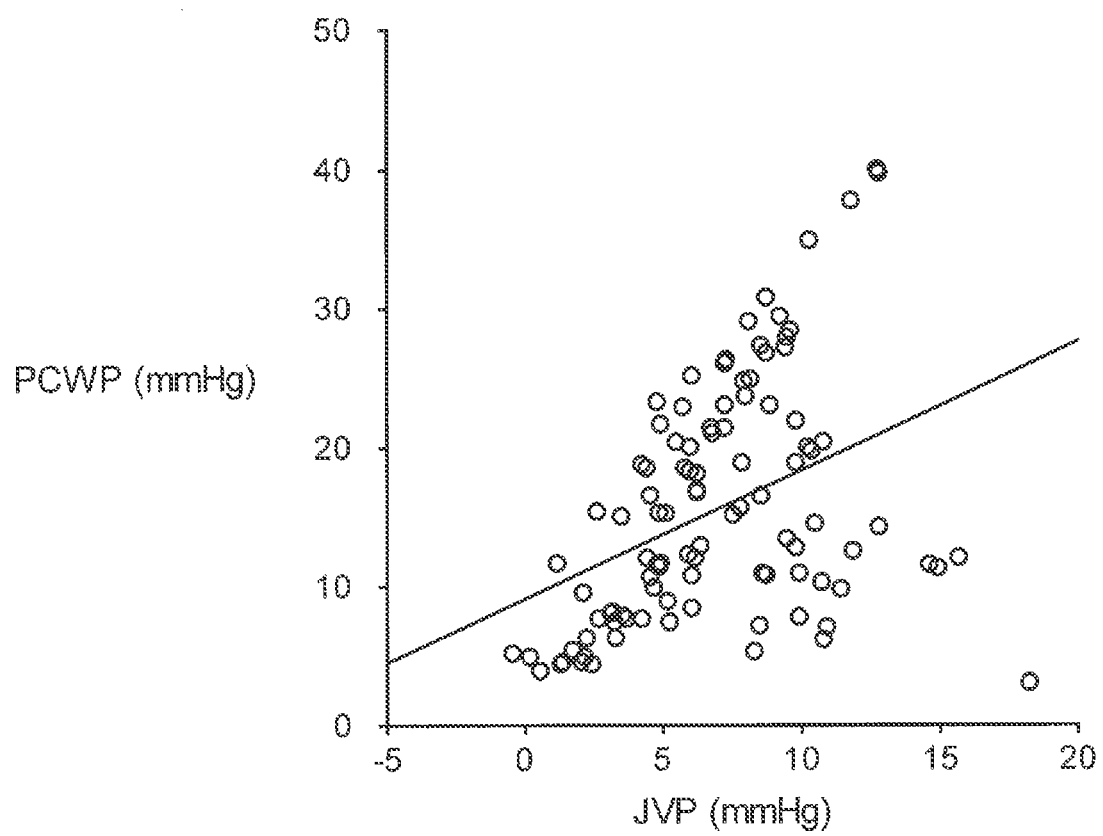
FIG. 5 is a graph showing the relationship between the pulmonary capillary wedge pressure (PCWP) and the jugular venous pressure (JVP) based on the results of preliminary experiments.

FIG. 5 is a graph showing the relationship between the pulmonary capillary wedge pressure (PCWP) and the jugular venous pressure (JVP) based on the results of the preliminary experiments. It is considered that the pulmonary capillary wedge pressure (PCWP) and the jugular venous pressure (JVP) have a statistically significant correlation. However, the degree of correlation was low ($R^2$=0.15), and a standard error of the regression formula was 7.9 mmHg.

Figure 6:
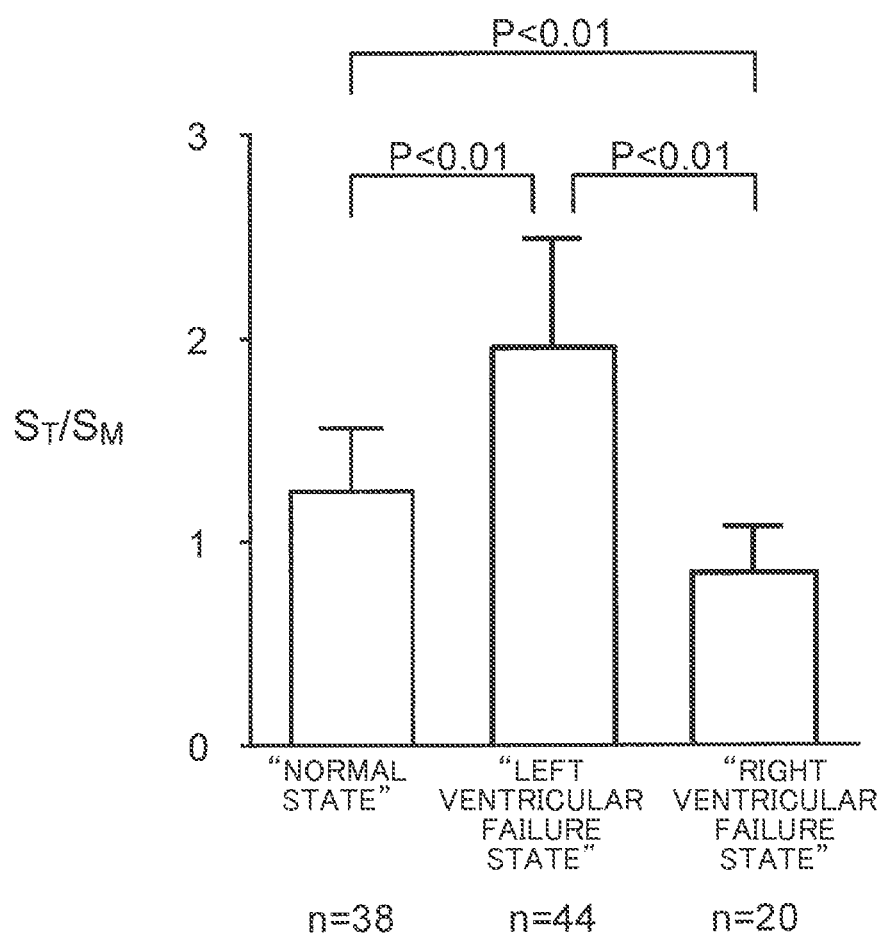
FIG. 6 is a graph showing the relationship between the state of the heart and the ratio of the peak systolic tricuspid annular velocity ($S_T$) to the peak systolic mitral annular velocity ($S_M$) based on the results of preliminary experiments.

FIG. 6 is a graph showing the relationship between the state of the heart and the ratio of the peak systolic tricuspid annular velocity ($S_T$) to the peak systolic mitral annular velocity ($S_M$). The ratio "$S_T/S_M$" in the left ventricular failure state was larger than that in the normal state, and the ratio "$S_T/S_M$" in the right ventricular failure state was smaller than that in the normal state. Specifically, the performance of the right ventricle was relatively improved in the left ventricular failure state, and the performance of the right ventricle was relatively decreased in the right ventricular failure state. The above results demonstrate that the theoretical basis for the left atrial pressure calculation method according to the embodiments of the invention is reasonable.

Figure 7:
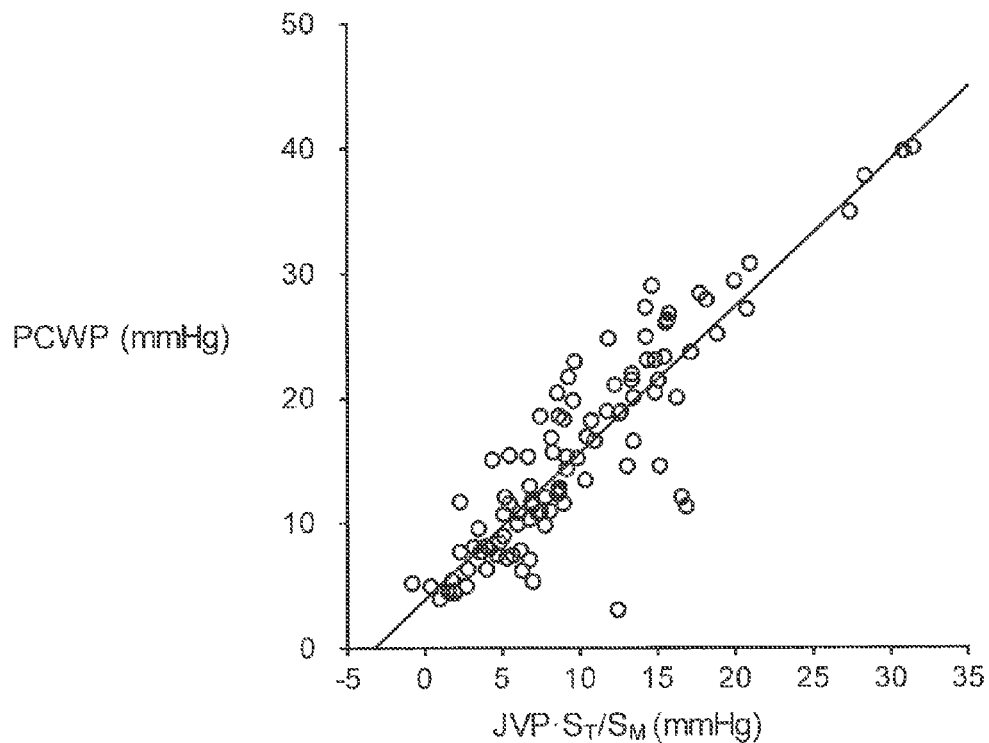
FIG. 7 is a graph showing the relationship between the pulmonary capillary wedge pressure (PCWP) and a value obtained by multiplying the jugular venous pressure (JVP) by the ratio "$S_T/S_M$" based on the results of preliminary experiments.

FIG. 7 is a graph showing the relationship between the pulmonary capillary wedge pressure (PCWP) and a value obtained by multiplying the jugular venous pressure (JVP) by the ratio "$S_T/S_M$". The degree of correlation was high ($R^2=0.80$), and a standard error of the regression formula was 3.8 mmHg (i.e., the error was roughly halved as compared with FIG. 5).

Figure 8:
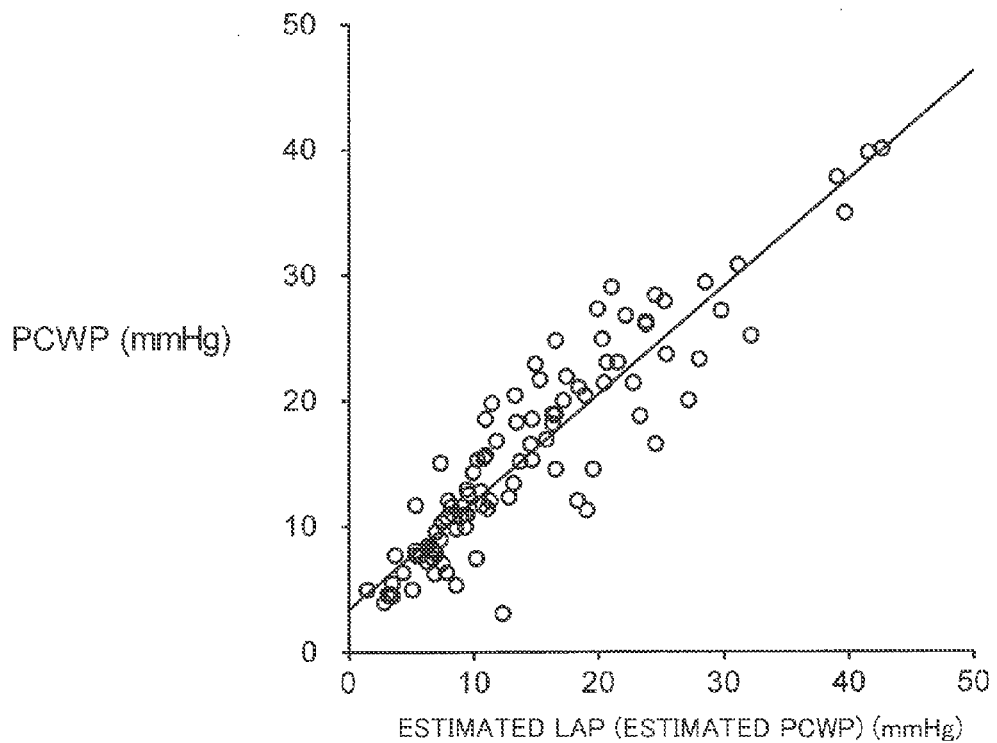
FIG. 8 is a graph showing the relationship between the pulmonary capillary wedge pressure (PCWP) and the left atrial pressure (LAP) estimated using the expression (J) based on the jugular venous pressure (JVP) and the ratio "$S_T/S_M$" measured by main experiments.

The constants C1, C2, and C3 in the expression (J) were regressively calculated from the measurements results obtained by the preliminary experiments. Six adult dogs other than those subjected to the preliminary experiments were subjected to main experiments in the left ventricular failure state or the right ventricular failure state. The constants determined by the preliminary experiments were prospectively applied to the main experiments. FIG. 8 is a graph showing the relationship between the pulmonary capillary wedge pressure (PCWP) and the estimated pulmonary capillary wedge pressure (PCWP) (i.e., left atrial pressure (LAP)) estimated using the expression (J) based on the constants determined by the preliminary experiments, the jugular venous pressure (JVP), and the ratio "$S_T/S_M$" measured by the main experiments.

The left atrial pressure (estimated LAP) estimated using the expression (J) had a high correlation with the measured pulmonary capillary wedge pressure (PCWP) ($R^2=0.84$), and a standard error of the regression formula was 2.4 mmHg. It was thus confirmed that the left atrial pressure estimation method according to the embodiments of the invention is effective.

According to the first embodiment, it is possible to implement a left atrial pressure measurement device that estimates the left atrial pressure based on the right atrial pressure, the peak systolic tricuspid annular velocity ($S_T$), and the peak systolic mitral annular velocity ($S_M$).

According to the first embodiment, when measuring the right atrial pressure, it is unnecessary to insert a catheter into the pulmonary artery through the jugular vein and the right atrium, differing from known pulmonary artery catheterization. Moreover, it is unnecessary to temporarily block the blood flow by wedging a balloon into the pulmonary artery. Therefore, the burden imposed on the subject can be reduced. Moreover, it is possible to estimate the left atrial pressure without requiring skill, differing from known pulmonary artery catheterization that requires skill to insert a catheter. These advantages contribute to the widespread use of the left atrial pressure measurement device in medical practice.

Modifications

The embodiments to which the invention is applied have been described above. Note that the invention is not limited thereto. The elements described in connection with the above embodiments may be appropriately modified or omitted, or other elements may be appropriately added without departing from the scope of the invention.

First Modification

Although the above embodiments have been described taking an example in which the left atrial pressure (LAP) is calculated using the expression (J), the left atrial pressure (LAP) may be estimated using the following expression (K).

$$\text{Left atrial pressure} = B1 \cdot \text{right atrial pressure} \cdot (S_T/S_M) + B2 \quad (K)$$

where, B1 and B2 are constants regressively determined by the preliminary experiments or the like.

Second Modification

Although the above embodiments have been described taking an example in which the right atrial pressure (RAP) is calculated based on the jugular venous pressure (JVP), the right atrial pressure (RAP) may be calculated from another biological information.

Figure 9:
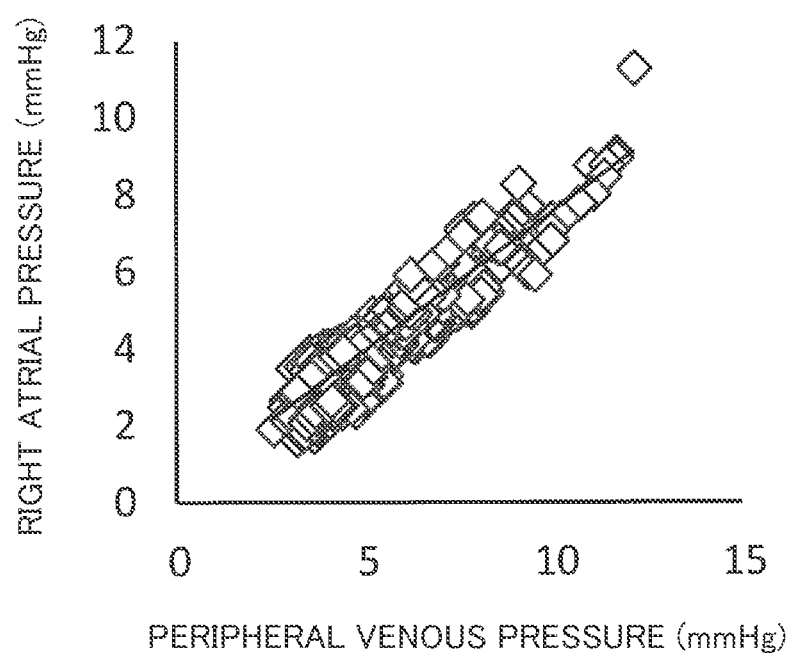
FIG. 9 is a graph showing the relationship between the peripheral venous pressure and the right atrial pressure.
Figure 10:
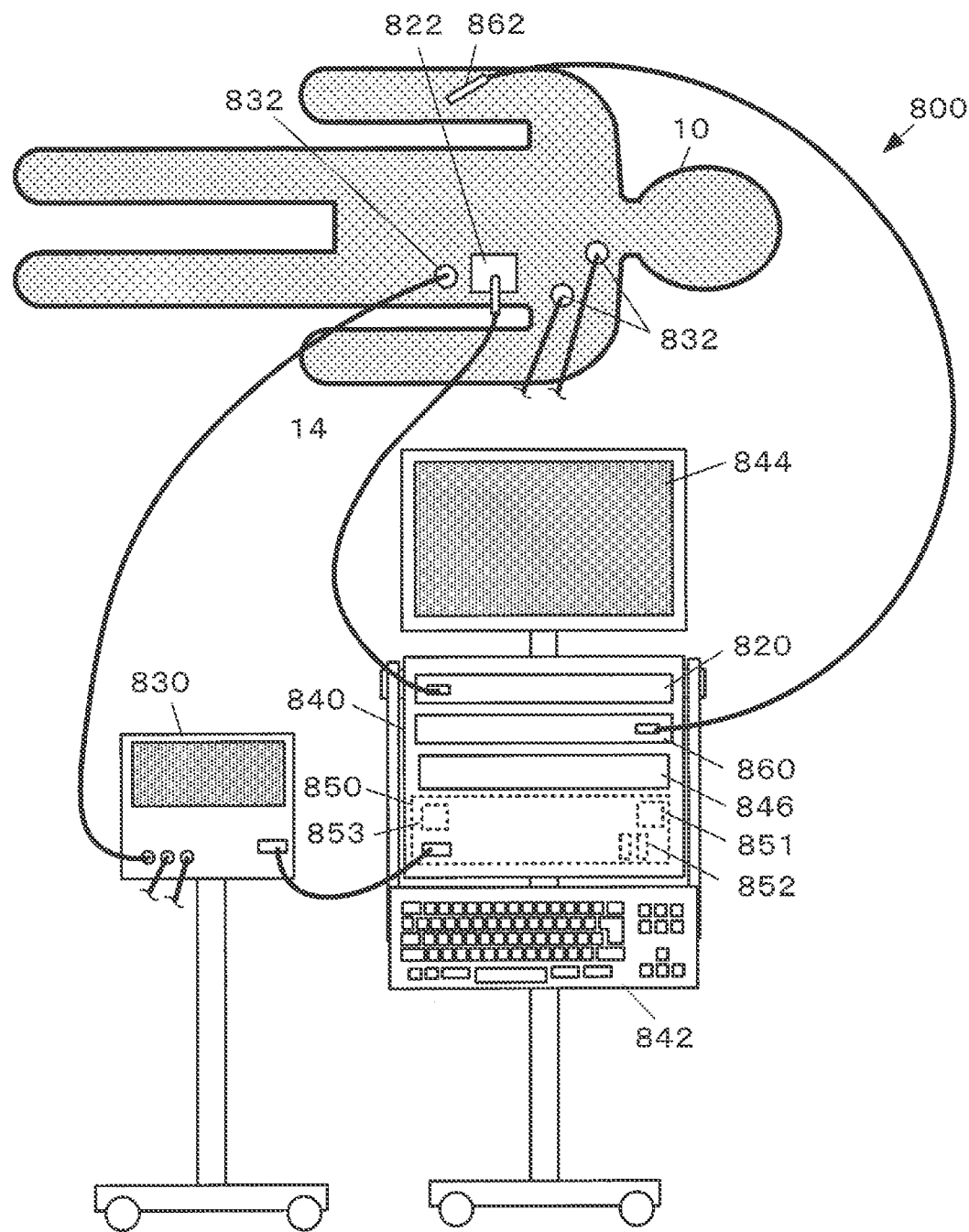
FIG. 10 is a view illustrating a system configuration example of a left atrial pressure measurement device according to a modification.

For example, the right atrial pressure (RAP) may be calculated from the peripheral venous pressure measured using a peripheral venous pressure measurement catheter. It has been known that the peripheral venous pressure has a correlation with the right atrial pressure (RAP) (see Intensive Care Med. 2004; 30: 627), and it was demonstrated by the animal experiments that the peripheral venous pressure and the right atrial pressure (RAP) have a high correlation (see FIG. 9, $R^2=0.8105$). Therefore, the jugular venous pressure measurement device 810 may be replaced with a peripheral venous pressure measuring device 860 that uses a peripheral venous pressure measurement catheter 862 (see FIG. 10). In this case, the right atrial pressure calculation section 204 calculates the right atrial pressure based on the peripheral venous pressure.

Third Modification

The peak systolic tricuspid annular velocity ($S_T$) and the peak systolic mitral annular velocity ($S_M$) may be replaced with the average systolic velocity of the tricuspid annulus 8 and the average systolic velocity of the mitral annulus 9. Likewise, the peak systolic tricuspid annular velocity ($S_T$) and the peak systolic mitral annular velocity ($S_M$) may be replaced with the peak systolic acceleration of the tricuspid annulus 8 and the peak systolic acceleration of the mitral annulus 9.

Although only some embodiments of the present invention have been described in detail above, those skilled in the art will readily appreciate that many modifications are possible in the embodiments without materially departing from the novel teachings and advantages of this invention. Accordingly, all such modifications are intended to be included within scope of this invention.

What is claimed is:

1. A left atrial pressure measurement method comprising:
causing a transthoracic echocardiographic device to acquire an ultrasonic echo using one or two pad-type ultrasonic probes attached to a chest of a subject to continuously measure a velocity of a tricuspid annulus and a velocity of a mitral annulus;
causing a heartbeat measurement device to continuously measure a heartbeat of the subject;
causing a processing device to calculate a relative ratio $S_T/S_M$ of the velocity of the tricuspid annulus to the velocity of the mitral annulus when the heartbeat is in a systolic phase, wherein $S_T$ is peak systolic tricuspid annular velocity and $S_M$ is peak systolic mitral annular velocity; and
causing the processing device to calculate a left atrial pressure based on an expression (J) or (K) using the relative ratio $S_T/S_M$ and a given right atrial pressure of the subject, $$\text{Left atrial pressure} = \text{EXP}[C1 \cdot \ln(\text{right atrial pressure}) + C2 \cdot \ln(S_T/S_M) + C3] \quad (J)$$

$$\text{Left atrial pressure} = B1 \cdot \text{right atrial pressure} \cdot (S_T/S_M) + B2 \quad (K)$$

where, C1, C2, C3, B1, and B2 are constants,
the left atrial pressure being calculated by measuring the velocity of the tricuspid annulus, the velocity of the mitral annulus, the heartbeat, and the right atrial pressure as measured values with respect to a heart of the subject.

2. The left atrial pressure measurement method as defined in claim 1,
the calculating of the relative ratio including calculating a relative ratio of a maximum value or an average value of the velocity of the tricuspid annulus in the systolic phase to a maximum value or an average value of the velocity of the mitral annulus in the systolic phase.

3. The left atrial pressure measurement method as defined in claim 1,
the calculating of the left atrial pressure including continuously calculating the left atrial pressure.

4. The left atrial pressure measurement method as defined in claim 1, further comprising:
measuring a jugular venous pressure or a peripheral venous pressure; and
determining the right atrial pressure from the measured jugular venous pressure or peripheral venous pressure.

5. A left atrial pressure measurement method comprising:
causing a transthoracic echocardiographic device to acquire an ultrasonic echo using one or two pad-type ultrasonic probes attached to a chest of a subject to continuously measure an acceleration of a tricuspid annulus and an acceleration of a mitral annulus;
causing a heartbeat measurement device to continuously measure a heartbeat of the subject;
causing a processing device to calculate a relative ratio $S_T/S_M$ of the acceleration of the tricuspid annulus to the acceleration of the mitral annulus when the heartbeat is in a systolic phase, wherein $S_T$ is peak systolic tricuspid annular acceleration and $S_M$ is peak systolic mitral annular acceleration; and
causing the processing device to calculate a left atrial pressure based on an expression (J) or (K) using the relative ratio $S_T/S_M$ and a given right atrial pressure of the subject, $$\text{Left atrial pressure} = \text{EXP}[C1 \cdot \ln(\text{right atrial pressure}) + C2 \cdot \ln(S_T/S_M) + C3] \quad \text{(J)}$$

$$\text{Left atrial pressure} = B1 \cdot \text{right atrial pressure} \cdot (S_T/S_M) + B2 \quad \text{(K)}$$

where, C1, C2, C3, B1, and B2 are constants,
the left atrial pressure being calculated by measuring the acceleration of the tricuspid annulus, the acceleration of the mitral annulus, the heartbeat, and the right atrial pressure as measured values with respect to a heart of the subject.

6. The left atrial pressure measurement method as defined in claim 5,
the calculating of the relative ratio including calculating a relative ratio of a maximum value or an average value of the acceleration of the tricuspid annulus in the systolic phase to a maximum value or an average value of the acceleration of the mitral annulus in the systolic phase.

7. The left atrial pressure measurement method as defined in claim 5,
the calculating of the left atrial pressure including continuously calculating the left atrial pressure.

8. A system that measures a left atrial pressure of a subject, the system comprising:
a transthoracic echocardiographic device that acquires an ultrasonic echo using one or two pad-type ultrasonic probes configured to be attached to a chest of the subject to continuously measure a velocity of a tricuspid annulus and a velocity of a mitral annulus;
a heartbeat measurement device that continuously measures a heartbeat of the subject; and
a processing device that calculates a relative ratio $S_T/S_M$ of the velocity of the tricuspid annulus to the velocity of the mitral annulus when the heartbeat is in a systolic phase, wherein $S_T$ is peak systolic tricuspid annular velocity and $S_M$ is peak systolic mitral annular velocity, and calculates the left atrial pressure based on an expression (J) or (K) using the relative ratio $S_T/S_M$ and a given right atrial pressure of the subject, $$\text{Left atrial pressure} = \text{EXP}[C1 \cdot \ln(\text{right atrial pressure}) + C2 \cdot \ln(S_T/S_M) + C3] \quad \text{(J)}$$

$$\text{Left atrial pressure} = B1 \cdot \text{right atrial pressure} \cdot (S_T/S_M) + B2 \quad \text{(K)}$$

where, C1, C2, C3, B1, and B2 are constants,
the left atrial pressure being calculated by measuring the velocity of the tricuspid annulus, the velocity of the mitral annulus, the heartbeat, and the right atrial pressure as measured values with respect to a heart of the subject.

9. A system that measures a left atrial pressure of a subject, the system comprising:
a transthoracic echocardiographic device that acquires an ultrasonic echo using one or two pad-type ultrasonic probes configured to be attached to a chest of the subject to continuously measure an acceleration of a tricuspid annulus and an acceleration of a mitral annulus;
a heartbeat measurement device that continuously measures a heartbeat of the subject; and
a processing device that calculates a relative ratio $S_T/S_M$ of the acceleration of the tricuspid annulus to the acceleration of the mitral annulus when the heartbeat is in a systolic phase, wherein $S_T$ is peak systolic tricuspid annular acceleration and $S_M$ is peak systolic mitral annular acceleration, and calculates the left atrial pressure based on an expression (J) or (K) using the relative ratio $S_T/S_M$ and a given right atrial pressure of the subject, $$\text{Left atrial pressure} = \text{EXP}[C1 \cdot \ln(\text{right atrial pressure}) + C2 \cdot \ln(S_T/S_M) + C3] \quad \text{(J)}$$

$$\text{Left atrial pressure} = B1 \cdot \text{right atrial pressure} \cdot (S_T/S_M) + B2 \quad \text{(K)}$$

where, C1, C2, C3, B1, and B2 are constants,
the left atrial pressure being calculated by measuring the acceleration of the tricuspid annulus, the acceleration of the mitral annulus, the heartbeat, and the right atrial pressure as measured values with respect to a heart of the subject.

* * * * *